United States Patent [19]

Chen et al.

[11] 4,048,309

[45] Sept. 13, 1977

[54] TOPICAL STEROID OINTMENT FORMULATIONS

[75] Inventors: James Ling Chen, East Brunswick; Jean M. Battaglia, North Brunswick, both of N.J.

[73] Assignee: E. R. Squibb & Sons, Inc., Princeton, N.J.

[21] Appl. No.: 660,964

[22] Filed: Feb. 24, 1976

[51] Int. Cl.$^2$ .............................................. A61K 31/56
[52] U.S. Cl. ................................................ 424/238
[58] Field of Search ........................................ 424/238

[56] References Cited

U.S. PATENT DOCUMENTS

| | | | |
|---|---|---|---|
| 3,758,686 | 9/1973 | Sieger et al. | 424/238 |
| 3,892,856 | 7/1975 | Hill et al. | 424/238 |
| 3,900,561 | 8/1975 | Davis | 424/238 |

*Primary Examiner*—Elbert L. Roberts
*Attorney, Agent, or Firm*—Lawrence S. Levinson; Merle J. Smith; Burton Rodney

[57] ABSTRACT

Steroid ointment formulations of the solution and biphasic types which are used as topical anti-inflammatory agents are provided wherein the steroid, such as 21-chloro-9α-fluoro-Δ$^4$-pregnene-11β,16α,17α-triol-3,20-dione 16,17-acetonide, is at least partially dissolved in a ricinoleate vehicle such as castor oil.

22 Claims, No Drawings

TOPICAL STEROID OINTMENT FORMULATIONS

The present invention relates to topical steroid ointment formulations which include one or more ricinoleates, such as castor oil, as a vehicle for the steroid.

Topical steroid formulations containing 21-chloro-9α-fluoro-Δ⁴-pregnene-11β,16α,17α-triol-3,20-dione 16,17-acetonide as the active ingredient are extensively employed in the treatment of skin disorders, such as dermatitis. To be therapeutically effective, the active ingredient must be in a molecular dispersion to facilitate desired percutaneous absorption which is particularly important in achieving a therapeutic response for the management of psoriasis. Unfortunately, the above steroid is insoluble in water (less than 0.0005% soluble) and is even less soluble in hydrocarbon vehicles such as mineral oil, petrolatum or polyethylene gelled mineral oil. Various organic solvents and solubilizers have been found to be good solvents for such steroid. However, they have been found to be unsuitable for commercial application for reasons such as their high volatility and low boiling points, their disagreeable odor, their "paint removing" property, and their undesirable skin reaction. Furthermore, various water-soluble emulsifiers and oil liquids or emollients have been suggested for use in preparing ointments and gels. However, because of the undesirably low solubility of the steroid in such vehicles, higher levels of these materials in topical products are required thereby increasing their cost and also adversely affecting their cosmetic elegance.

Accordingly, in view of the above considerations, it is seen that a need exists for a suitable vehicle capable of solubilizing a sufficient amount of the steroid so that it may be employed in a topical ointment formulation, while being dermatologically beneficial, stable, and pharmaceutically acceptable.

In accordance with the present invention, it has now been found that ricinoleates, such as castor oil, are excellent vehicles for 21-chloro-9α-fluoro-Δ⁴-pregnene-11β,16α,17α-triol-3,20-dione 16,17-acetonide as well as for other steroids such as 21-chloro-9-fluoro-2′,3′-dihydro-11β-hydroxy-5′-phenylpregna-1,4-dieno[16α,17-b][1,4]dioxin-3,20-dione dichloro methane solvate (1:1), and 9α-fluoro-11β, 16α,17,21-tetrahydroxy-pregna-1,4-diene-3,20-dione 16,17-acetonide The topical steroid ointment formulations of the invention comprise a steroid as described above, a ricinoleate vehicle and oleaginous material, and optionally a wax.

The term "ointment" or "ointment formulation" as employed herein includes non-aqueous formulations such as gels, ointments, lipophilic sticks, and the like.

The ricinoleate vehicle may comprise one or more ricinoleates alone or in admixture with fatty acids or other vehicles and may be present in amounts within the range of from about 0.5 to about 70% by weight and preferably from about 1 to about 15% by weight of the steroid formulation depending upon the particular steroid employed, except that in the case of a lipophilic stick, from 50 to 70% by weight ricinoleate is employed. The preferred rininoleate suitable for use herein is castor oil, that is, ricinus oil or triglyceride of fatty acids, the fatty acid composition being approximately 87% glyceryl ricinoleate, 7% oleic acid, 3% linoleate, 2% palmitate, 1% stearate and trace amounts of other compounds such as dihydroxystearic acid. Other examples of suitable ricinoleates include, but are not limited to, propylene glycol monoricinoleate, diglycol ricinoleate, and water-insoluble polyethylene glycol ricinoleates and the like.

The steroid will be present in an amount of from about 0.005 to about 0.6% by weight, and preferably from about 0.025 to about 0.2% based on the total weight of the composition, depending upon the type of steroid employed and its solubility in the ricinoleate vehicle. As will be seen hereinafter, other active ingredients may be employed in conjunction with the steroid. In such case, the other active ingredients, such as econazole, nystatin, neomycins, gramicidins and the like, and mixtures thereof, may be employed in amounts up to and even greater than 3%.

The oleaginous material will generally be present in an amount within the range of from about 30 to about 99% by weight, and preferably from about 50 to about 90% by weight.

The topical steroid non-aqueous formulations of the invention may take the form of an ointment, gel, lipophilic (molded) stick, and the like, that is, those formulations which include a large oil phase. Furthermore, the ointments of the invention may include the steroid component "all-in-solution" in the oil phase so that substantially no steroid crystallizes out at room temperature. Alternatively, the ointment may comprise a biphasic system, that is, a system wherein a portion (from about 30 to about 75% by weight) of the steroid is in solution in the ricinoleate oil phase and the remainder of the steroid is dispersed in the oleaginous material. The ricinoleate preferably contains from about 80 to about 100% of that amount of steroid required to form a saturated solution of the steroid in the ricinoleate, at room temperature.

With regard to the formulations of the invention where the steroid is to be all-in-solution, the ointment will contain from about 0.005 to about 0.6% and preferably from about 0.025 to about 0.2% by weight of the active ingredient based on the weight of the entire cream formulation, and from about 0.5 to about 16% and preferably from about 1 to about 12% by weight of the ricinoleate based on the weight of the entire ointment formulation (and up to 75% by weight ricinoleate in the case of the lipophilic stick) and depending upon the solubility of the particular steroid in the particular ricinoleate employed. The all-in-solution ointment formulation (exclusive of the gel and lipophilic stick) will also include, in addition to the steroid and ricinoleate, from about 85 to about 99% and preferably from about 85 to about 95% by weight of oleaginous material based on the weight of the entire formulation. The formulation may also optionally include an opacifying agent, such as titanium dioxide, serving as indicator for homogeneity of dispersion, in an amount within the range of from about 0.2 to about 1% and preferably from about 0.3 to about 0.8% by weight based on the entire formulation. An antioxidant may also optionally be included in an amount within the range of from about 0.005 to about 0.04% and preferably from about 0.01 to about 0.03% by weight based on the entire formulation.

With regard to the ointment formulation of the invention (exclusive of the gel and lipophilic stick) in the form of the biphasic system, the ointment will contain from about 0.005 to about 0.6% and preferably from about 0.025 to about 0.2% by weight of the active ingredient based on the weight of the entire formulation, and from about 0.5 to about 14% and preferably from about 1 to about 12% by weight of the ricinoleate based on the weight of the entire formulation, depending upon the solubility of the particular steroid in the particular ricinoleate employed. The biphasic formulation will also include, in addition to the steroid and ricinoleate, from about 90 to about 97% and preferably from about 94 to about 96% by weight of oleaginous material based on the weight of the entire formulation. The biphasic formulation may also optionally include a coloring agent and/or antioxidant in the amounts described above.

Examples of oleaginous material suitable for use herein are petrolatum, other ricinoleate immiscible oily material and mineral oil thickened or gelled with polyethylene, or high molecular weight paraffin waxes or mono and diglycerides of fatty acids gelled with high molecular weight fatty acids and/or polyamide complex of hydroxystearate. Petrolatum (petroleum jelly) is a purified mixture of semi-solid hydrocarbons from petroleum having a melting point of from about 45° to about 65° C, preferably from about 50° to about 60° C. When the mixture of steroid and ricinoleate is mechanically dispersed in the oleaginous material, the latter may be mineral oil thickened with polyethylene as disclosed in U.S. Pat. Nos. 2,627,938, 2,628,187, 2,628,205 and 3,733,403. The disclosures of the foregoing patents are incorporated herein by reference.

The all-in-solution ointment may simply be prepared by dissolving the steroid in the ricinoleate with gentle heat not over 90° C, cooling to room temperature and then incorporating the same into the oleaginous material by slow mixing until homogeneous.

The biphasic ointment may be prepared by mixing a portion of micronized steroid (e.g., 10–90% of total amount of steroid) with an opacifying agent, such as titanium dioxide, thoroughly dispersing such mixture with an oleaginous material (in softened condition; e.g., 5 to 20% of total amount of oleaginous material) to form a dispersed steroid concentrate; mixing the concentrate into the remainder of the oleaginous material; adding to the above mixture a solution of the remainder of the steroid in the ricinoleate vehicle at a temperature comparable to that of the oleaginous material; and continue mixing until the mixture congeals. It will be appreciated that where petrolatum or other relatively stiff oleaginous material is used, the oleaginous material should be heated to soften the same and thereby facilitate mixing thereof with the other ingredients. Furthermore, it may be necessary to employ heat to facilitate dissolution of the steroid in the ricinoleate vehicle.

The gel formulation of the invention is preferably in the form of a lipophilic clear gel, and will contain from about 0.005 to about 0.6% and preferably from about 0.025 to about 0.2% by weight of the steroid based on the weight of the entire formulation, and from about 0.5 to about 16% and preferably from about 1 to about 12% by weight of the ricinoleate based on the weight of the entire formulation, depending upon the solubility of the particular steroid in the particular ricinoleate employed. The gel formulation will also include from about 85 to about 94% and preferably from about 88 to about 91% by weight of the oleaginous material. The formulation may also optionally include a surfactant, such as Span 65 (sorbitan tristearate), as well as Span 60 (sorbitan monostearate), Span 40 (sorbitan monopalmitate), butylene glycol distearate in amounts up to about 8% by weight based on the entire formulation. An antioxidant such as butylated hydroxyanisole or butylated hydroxytoluene may also optionally be included in amounts up to about 0.1% and preferably up to about 0.05% by weight based on the entire formulation.

In the non-aqueous gel formulation of the invention, the oleaginous material includes mineral oil gelled with waxes such as high molecular weight paraffin wax (Paraflint RG), mono and diglycerides of fatty acids such as Arlacel 186 (Atlas Co.) as well as propylene glycol isostearate (Emery 2389A) or isostearyl alcohol (Adol 66), gelled with high molecular weight fatty acids such as Emery 865A, (Emery Industries) and/or polyamide complex of hydroxystearate (Acrowax, Glyco).

With regard to specific steroid ointment or gel formulations, where 21-chloro-9α-fluoro-Δ⁴-pregnene-11β,16α,17α-triol-3,20-dione 16,17-acetonide is employed in all-in-solution ointments, the ricinoleate vehicle will be preferably employed in an amount within the range of from about 3 to about 16% by weight and more preferaly within the range of from about 5 to about 12% by weight depending upon the amount of steroid employed; in the case of biphasic formulations containing the above steroid, the ricinoleate vehicle will be preferably employed in an amount within the range of from about 3 to about 14% by weight and more preferably from about 5 to about 10% by weight depending upon the amount of steroid employed.

Where 21-chloro-9-fluoro-2',3'-dihydro-11β-hydroxy-5'-phenylpregna-1,4-dieno[16α,17-b][1,4]dioxin-3,20-dione dichloro methane solvate (1:1) is employed in all-in-solution ointments, the ricinoleate vehicle will be preferably employed in an amount within the range of from about 0.5 to about 5% by weight and more preferably within the range of from about 1 to about 4% by weight depending upon the amount of steroid employed; in the case of biphasic formulations containing the above steroid, the ricinoleate vehicle will be preferably employed in an amount within the range of from about 0.5 to about 4% by weight and more preferably from about 1 to about 3% by weight depending upon the amount of steroid employed.

Where 9α-fluoro-11β,16α,17,21-tetrahydroxypregna-1,4-diene-3,20-dione 16,17-acetonide is employed in all-in-solution ointments, the ricinoleate vehicle will be preferably employed in an amount within the range of from about 3 to about 16% by weight and more preferably within the range of from about 5 to about 12% by weight depending upon the amount of steroid employed; in the case of biphasic formulations containing the above steroid, the ricinoleate vehicle will be preferably employed in an amount within the range of from about 3 to about 14% by weight and more preferably from about 5 to about 10% by weight depending upon the amount of steroid employed.

The lipophilic stick of the invention may contain from about 0.005 to about 0.6%, and preferably from about 0.025 to about 0.2% by weight of the steroid, and from about 50 to about 70% and preferably from about 55 to about 65% by weight of the ricinoleate (regardless of which is employed) and from about 20 to about 50% and preferably from about 25 to about 45% by weight oleaginous material. Oleaginous materials which may be employed include high melting waxes, such as carnauba wax, in amounts ranging from about 6 to about 10% and preferably from about 7 to about 9%, beeswax in amounts ranging from about 14 to about 18% and preferably from about 15 to about 17%, as well as petrolatum in amounts ranging from about 2 to about 5% and preferably from about 3 to about 4%, and isostearyl neo pentanoate (Ceraphyl 375, Van Dyk) in amounts ranging from about 8 to about 11% and preferably from about 9 to about 10.5%.

The following examples illustrate preferred embodiments of the present invention without, however, limiting the same thereto. All temperatures are expressed in degrees Centigrade.

EXAMPLE 1

Ointment, 0.025% (all-in-solution)

21-chloro-9α-fluoro-Δ$^4$-pregnene-11β,16α,17α-triol-3,20-dione 16,17-acetonide, Micronized: 0.025 gm.
Castor Oil, U.S.P.: 10.0 gm.
Titanium Dioxide: 0.5 gm.
Plastibase 50W (mineral oil (95%) gelled with polyethylene (5%) sufficient to make 100.0 gm.

The steroid is dissolved in castor oil with gentle heat not over 90° C. The solution is cooled to room temperature and titanium dioxide is dispersed homogeneously into the oil. The suspension is incorporated into the Plastibase by slow rate of mixing until homogeneous to form the ointment.

EXAMPLE 2

Ointment, 0.025% (biphasic)

21-chloro-9α-fluoro-Δ$^4$-pregnene-11β,16α,17α-triol-3,20-dione 16,17-acetonide, Micronized: 0.025 gm.
Castor Oil, U.S.P.: 5.0 gm.
Titanium Dioxide: 0.5 gm.
Plastibase 50W, sufficient to make 100.0 gm.

0.0125 gm of steroid is dissolved in castor oil by gentle heating not over 90° C. The solution is cooled to room temperature and mixed with 0.2 gm of titanium dioxide. 0.0125 gm of the steroid is mixed with 0.3 gm of titanium dioxide and dispersed into about 1 gm of Plastibase homogeneously. The resulting concentrate is dispersed geometrically into the remainder of the Plastibase.

The castor oil dispersion is incorporated with about an equal amount of the Plastibase dispersion and mixed thoroughly. The remainder of the Plastibase dispersion is mixed with the castor oil dispersion until a homogeneous mixture is obtained (for about 20 to 30 minutes).

EXAMPLE 3

Lipophilic Clear Gel, 0.025% (all-in-solution)

21-chloro-9α-fluoro-Δ$^4$-pregnene-11β,16α,17α-triol-3,20-dione 16,17-acetonide, Micronized: 0.025 gm.
Castor Oil, U.S.P.: 10.0 gm.
Mineral Oil, U.S.P.: 80.375 gm.
Paraflint RG (High melting paraffin wax), Moore and Munger 6.0 gm.
Span 65 (Sorbitan tristearate, ICI) 3.6 gm.

Paraflint RG and Span 65 are melted and heated to 100° C. The molten mixture is incorporated in hot (100° C) mineral oil and mixed well. The temperature of the oil is quickly brought to 50° C to form a gel.

The steroid is dissolved in castor oil by gentle heat, the oil is cooled to room temperature and then is incorporated in the gel homogeneously.

EXAMPLE 4

Lipophilic Clear Gel, 0.025% (all-in-solution)

21-chloro-9α-fluoro-Δ$^4$-pregnene-11β,16α,17α-triol-3,20-dione 16,17-acetonide, Micronized: 0.025 gm.
Castor Oil, U.S.P.: 10.0 gm.

Arlacel 186, Atlas Co. (Mono and diglycerides of fatty acids): 71.975 gm.
Acrowax, Glyco Product (Polyamide complex of hydroxystearate): 8.0 gm.
Emery 865A, Emery Indus. (long chain alpha methyl branched fatty acids $C_{29}$ and higher): 4.0 gm.
Butylene Glycol Distearate 6.0 gm.

The steroid is discharged in the castor oil and heated to form a solution which is then cooled to room temperature. Acrowax, butylene glycol distearate, and Emery 865A are melted and dissolved in Arlacel 186. The melt is mixed well and cooled quickly on chilled metal plate to form a gel. The steroid-castor oil solution is incorporated into the gel and mixed until homogeneous.

EXAMPLE 5

Lipophilic Stick 21-chloro-9α-fluoro-Δ$^4$-pregnene-11β,16α,17α-triol-3,20-dione 16,17-acetonide, Micronized: 0.1 gm.
Castor Oil, U.S.P.: 60.0 gm.
Carnauba Wax: 8.0 gm.
Beeswax 16.0 gm.
Petrolatum: 3.4 gm.
Ceraphyl 375, Van Dyk (Isostearyl Neo Pentanoate): 10.0 gm.

The steroid is dissolved in castor oil with gentle heat not over 90° C. A molten mixture of the remaining ingredients is added to the above solution at 90° C. The mixture is poured into a mold and chilled to solidify the mixture to a stick.

EXAMPLE 6

Ointment, 0.025% (all-in-solution)

21-chloro-9-fluoro-2',3'-dihydro-11β-hydroxy-5'-phenylpregna-1,4-dieno-[16α,17-b][1,4]dioxin-3,20-dione: dichloro methane solvate (1:1): 0.025 gm.
Castor oil, U.S.P.: 3.0 gm.
Titanium Dioxide: 0.5 gm.
Plastibase 50W (mineral oil) (95%) gelled with polyethylene (5%) sufficient to make 100.0 gm.

The steroid is dissolved in castor oil with gentle heat not over 90° C. The solution is cooled to room temperature and titanium dioxide is dispersed homogeneously into the oil. The suspension is incorporated into the Plastibase by slow rate of mixing until homogeneous to form the ointment.

EXAMPLE 7

Ointment, 0.025% (biphasic)

21-chloro-9-fluoro-2',3'-dihydro-11β-hydroxy-5'-phenylpregna-1,4-dieno[16α,17-b][1,4]dioxin-3,20-dione: dichloro methane solvate (1:1): 0.025 gm.
Castor Oil, U.S.P.: 1.5 gm.
Titanium Dioxide: 0.5 gm.
Plastibase 50W, sufficient to make 100.0 gm.

0.0125 gm of steroid is dissolved in castor oil by gentle heating not over 90° C. The solution is cooled to room temperature and mixed with 0.2 gm of titanium dioxide. 0.0125 gm of the steroid is mixed with 0.3 gm of titanium dioxide and dispersed into about 1 gm of Plastibase homogeneously. The resulting concentrate is dispersed geometrically into the remainder of the Plastibase.

The castor oil dispersion if incorporated with about an equal amount of the Plastibase dispersion and mixed thoroughly. The remainder of the Plastibase dispersion is mixed with the castor oil dispersion until a homogeneous mixture is obtained (for about 20 to 30 minutes).

EXAMPLE 8

Lipophilic Clear Gel, 0.025% (all-in-solution)

21-chloro-9-fluoro-2',3'-dihydro-11β-hydroxy-5'-phenylpregna-1,4-dieno[16α,17-b][1,4]dioxin-3,20-dione:dichloro methane solvate (1:1): 0.025 gm.
Castor Oil, U.S.P.: 3.0 gm.
Mineral Oil, U.S.P.: 80.375 gm.
Paraflint RG (High melting paraffin wax), Moore and Munger: 6.0 gm.
Span 65 (Sorbitan tristearate, ICI): 3.6 gm.

Paraflint RG and Span 65 are melted and heated to 100° C. The molten mixture is incorporated in hot (100° C) mineral oil and mixed well. The temperature of the oil is quickly brought to 50° C to form a gel.

The steroid is dissolved in castor oil by gentle heat, the oil is cooled to room temperature and then is incorporated in the gel homogeneously.

EXAMPLE 9

Lipophilic Clear Gel, 0.025% (all-in-solution)

21-chloro-9-fluoro-2',3'-dihydro-11β-hydroxy-5'-phenylpregna-1,4-dieno[16α,17-b][1,4]dioxin-3,20-dione:dichloro methane solvate (1:1): 0.025 gm.
Castor Oil, U.S.P.: 6.0 gm.
Arlacel 186, Atlas Co. (Mono and diglycerides of fatty acids): 71,975 gm.
Acrowax, Glyco Product (Polyamide complex of hydroxystearate): 8.0 gm.
Emery 865A, Emery Indus. (High mol. wt. fatty acid): 4.0 gm.
Butylene Glycol Distearate: 6.0 gm.

The steroid is dispersed in the castor oil and heated to form a solution which is then cooled to room temperature. Acrowax, butylene glycol distearate, and Emery 865A are melted and dissolved in Arlacel 186. The melt is mixed well and cooled quickly on chilled metal plate to form a gel. The steroid-castor oil solution is incorporated into the gel and mixed until homogeneous.

EXAMPLE 10

Lipophilic Stick 21-chloro-9-fluoro-2',3'-dihydro-11β-hydroxy-5'-phenylpregna-1,4-dieno[16α,17-b][1,4]dioxin-3,20-dione:dichloro methane solvate (1:1): 0.025 gm.
Castor Oil, U.S.P.: 60.0 gm.
Carnauba Wax: 8.0 gm.
Beeswax: 16.0 gm.
Petrolatum: 3.4 gm.
Ceraphyl 375, Van Dyk (Isostearyl Neo Pentanoate): 10.0 gm.

The steroid is dissolved in castor oil with gentle heat not over 90° C. A molten mixture of the measuring ingredients is added to the above solution at 90° C. The mixture is poured into a mold and chilled to solidify the mixture to a stick.

EXAMPLE 11

Ointment, 0.025% (all-in-solution)

9α-fluoro-11β,16α,17,21-tetrahydroxypregna-1,4-diene-3,20-dione 16,17-acetonide: 0.025 gm.
Castor Oil, U.S.P.: 10.0 gm.
Titanium Dioxide: 0.5 gm.
Plastibase 50W (mineral oil) (95%) gelled with polyethylene (5%) sufficient to make 100.0 gm.

The steroid is dissolved in castor oil with gentle heat not over 90° C. The solution is cooled to room temperature and titanium dioxide is dispersed homogeneously into the oil. The suspension is incorporated into the Plastibase by slow rate of mixing until homogeneous to form the ointment.

EXAMPLE 12

Ointment, 0.025% (biphasic)

9α-fluoro-11β,16α,17,21-tetrahydroxypregna-1,4-diene-3,20-dione 16,17-acetonide: 0.025 gm.
Castor Oil, U.S.P. 5.0 gm.
Titanium Dioxide: 0.5 gm.
Plastibase 50W, sufficient to make 100.0 gm.

0.0125 gm of steroid is dissolved in castor oil by gentle heating not over 90° C. The solution is cooled to room temperature and mixed with 0.2 gm of titanium dioxide. 0.0125 gm of the steroid is mixed with 0.3 gm of titanium dioxide and dispersed into about 1 gm of Plastibase homogeneously. The resulting concentrate is dispersed geometrically into the remainder of the Plastibase.

The castor oil dispersion is incorporated with about an equal amount of the Plastibase dispersion and mixed thoroughly. The remainder of the Plastibase dispersion is mixed with the castor oil dispersion until a homogeneous mixture is obtained (for about 20 to 30 minutes).

EXAMPLE 13

Lipophilic Clear Gel, 0.025% (all-in-solution)

9α-fluoro-11β,16α,17,21-tetrahydroxypregna-1,4-diene-3,20-dione 16,17-acetonide: 0.025 gm.
Castor Oil, U.S.P.: 10.0 gm.
Mineral Oil, U.S.P.: 80.375 gm.
Paraflint RG (High melting paraffin wax), Moore and Munger: 6.0 gm.
Span 65 (Sorbitan tristearate, ICI): 3.6 gm.

Paraflint RG and Span 65 are melted and heated to 100° C. The molten mixture is incorporated in hot (100° C) mineral oil and mixed well. The temperature of the oil is quickly brought to 50° C to form a gel.

The steroid is dissolved in castor oil by gentle heat, the oil is cooled to room temperature and then is incorporated in the gel homogeneously.

EXAMPLE 14

Lipophilic Clear Gel, 0.025% (all-in-solution)

9α-fluoro-11β,16α,17,21-tetrahydroxypregna-1,4-diene-3,20-dione 16,17-acetonide: 0.025 gm.
Castor Oil, U.S.P.: 10.0 gm.
Arlacel 186, Atlas Co. (Mono and diglycerides of fatty acids): 71,975 gm.
Acrowax, Glyco Product (Polyamide complex of hydroxystearate): 8.0 gm.
Emery 865A, Emery Indus. (High mol. wt. fatty acid): 4.0 gm.
Butylene Glycol Distearate: 6.0 gm.

The steroid is dispersed in the castor oil and heated to form a solution which is then cooled to room temperature. Acrowax, butylene glycol distearate, and Emery 865A are melted and dissolved in Arlacel 186. The melt is mixed well and cooled quickly on chilled metal plate to form a gel. The steroid-castor oil solution is incorporated into the gel and mixed until homogeneous.

EXAMPLE 15

Lipophilic Stick

9α-fluoro-11β,16α,17,21-tetrahydroxypregna-1,4-diene-3,20-dione 16,17-acetonide: 0.025 gm.
Castor Oil, U.S.P.: 60.0 gm.
Carnauba Wax: 8.0 gm.
Beeswax: 16.0 gm.
Petrolatum: 3.4 gm.
Ceraphyl 375, Van Dyk (Isostearyl Neo Pentanoate): 10.0 gm.

The steroid is dissolved in castor oil with gentle heat not over 90° C. A molten mixture of the remaining ingredients is added to the above solution at 90° C. The mixture is poured into a mold and chilled to solidify the mixture to a stick.

What is claimed is:

1. A non-aqueous composition for topical application in the form of an ointment, gel or lipophilic stick comprising at least one steroid selected from the group consisting of 21-chloro-9α-fluoro-Δ⁴-pregnene-11β,16α,17α-triol-3,20-dione 16,17-acetonide; 21-chloro-9-fluoro-2',3'-dihydro-11β-hydroxy-5'-phenyl-pregna-1,4-dieno[16α,17-b][1,4]dioxin3,20-dione:dichloro methane solvate (1:1), and 9α-fluoro-11β,16α,17,21-tetrahydroxy-pregna-1,4-diene-3,20-dione 16,17-acetonide, a ricinoleate vehicle in which said steroid is at least partially soluble, and an oleaginous material, said oleaginous material is selected from the group consisting of petrolatum, mineral oil thickened or gelled with polyethylene, high molecular weight paraffin waxes, mono and diglycerides of fatty acids gelled with high molecular weight fatty acids or polyamide complex of hydroxystearate, propylene glycol isostearate or isostearyl alcohol gelled with high molecular weight fatty acids and mixtures thereof.

2. The composition as defined in claim 1 wherein said ricinoleate is castor oil.

3. The composition as defined in claim 1 wherein said steroid is present in an amount within the range of from about 0.005 to about 0.6% by weight of the composition, said ricinoleate vehicle is present in an amount within the range of from about 0.5 to about 70% by weight of the composition, and said oleaginous material is present in an amount within the range of from about 30 to about 99% by weight of the composition.

4. The composition as defined in claim 3 further including one or more antioxidants.

5. A composition as defined in claim 1 in the form of an ointment wherein said steroid is all-in-solution, and said steroid is present in an amount within the range of from about 0.005 to about 0.6% by weight of the composition, said ricinoleate is present in an amount within the range of from about 20% by weight of the composition, and said oleaginous material is present in an amount within the range of from about 80 to about 97% by weight of the composition 6. The composition as defined in claim 5 wherein said ricinoleate is castor oil.

7. A composition as defined in claim 1 in the form of an ointment of the biphasic type, wherein said steroid is present in an amount within the range from about 0.005 to about 0.6% by weight of the composition, said ricinoleate is present in an amount within the range of from about 0.5 to about 14% by weight of the composition, said oleaginous material is present in an amount within the range of from about 90 to about 98% by weight of the composition.

8. The composition as defined in claim 7 wherein said ricinoleate is castor oil.

9. A composition useful as a vehicle for steroids in the form of a clear lipophilic gel comprising a ricinoleate and an oleaginous material, said ricinoleate being present in an amount within the range of from about 0.5 to about 16% by weight of the composition, said oleaginous material being present in an amount within the range of from about 85 to about 94% by weight of the composition and comprising petrolatum, a mixture of mineral oil gelled with polyethylene, paraffin wax or a mixture of mono and diglycerides of fatty acids gelled with polyamide complex of hydroxystearate or high molecular weight fatty acids as a mixture having a molecular weight of at least 450 having a melting range of 67°–73° C, and a steroid present in an amount within the range of from about 0.005 to about 0.6% by weight of the total composition, said steroid being selected from the group consisting of 21-chloro-9α-fluoro-Δ⁴-pregnene-11β,16α,17α-triol-3,20-dione 16,17-acetonide; 21-chloro-9-fluoro-2',3'-dihydro-11β-hydroxy-5'-phenyl-pregna-1,4-dieno[16α,17-b][1,4]dioxin-3,20-dione:dichloro methane solvate (1:1), and 9α-fluoro-11β,16α,17,21-tetrahydroxy-pregna-1,4-diene-3,20-dione 16,17-acetonide.

10. The composition as defined in claim 9 wherein said ricinoleate is castor oil.

11. The composition as defined in claim 9 comprising castor oil, high melting paraffin wax and sorbitan tristearate.

12. The composition as defined in claim 9 comprising mono and diglycerides of fatty acids, polyamide complex of hydroxystearate, a mixture of long-chain alpha methyl branched acids $C_{29}$ and higher and butylene glycol distearate.

13. A composition useful as a vehicle for steroids in the form of a lipophilic stick, comprising a ricinoleate and an oleaginous material selected from the group consisting of petrolatum, mineral oil thickened or gelled with polyethylene, high molecular weight paraffin waxes, mono and diglycerides of fatty acids gelled with high molecular weight fatty acids or polyamide complex of hydroxystearate, propylene glycol isostearate or isostearyl alcohol gelled with high molecular weight fatty acids and mixtures thereof, said ricinoleate being present in an amount within the range of from about 50 to about 70% by weight of the composition and said oleaginous material being present in an amount within the range of from about 20 to about 50% by weight of the composition, and a steroid present in an amount within the range of from about 0.005 to about 0.6% by weight of the total composition said steroid being selected from the group consisting of 21-chloro-9-fluoro-2',3'-dihydro-11β-hydroxy-5'-phenylpregna-1,4-dieno[-16α,17-b][1,4]dioxin-3,20-dione:dichloro methane solvate (1:1), 21-chloro-9α-fluoro-Δ⁴-pregnene-11β,16α,-17α-triol-3,20-dione 16,17-acetonide, and 9α-fluoro-11β,16α,17,21-tetrahydroxypregna-1,4-diene-3,20-dione 16,17-acetonide.

14. The composition as defined in claim 13 wherein said ricinoleate is castor oil and said oleaginous material is a mixture of carnauba wax, beeswax and petrolatum and further including isostearyl neopentanoate as a slip agent.

15. A composition as defined in claim 12 wherein said oleaginous material is petrolatum or mineral oil gelled with polyethylene.

16. A composition as defined in claim 1 further including from about 0.5 to about 2% by weight of econazole, gramicidin, neomycin, nystatin, or mixtures thereof.

17. A method of treating dermatitis, which comprises administering topically an effective amount of a composition as defined in claim 1.

18. A method of treating dermatitis, which comprises administering topically an effective amount of a composition as defined in claim 3.

19. A method of treating dermatitis, which comprises administering topically an effective amount of a composition as defined in claim 5.

20. A method of treating dermatitis, which comprises administering topically an effective amount of a composition as defined in claim 7.

21. A method of treating dermatitis, which comprises administering topically an effective amount of a composition as defined in claim 1.

22. A method of treating dermatits, which comprises administering topically an effective amount of a composition as defined in claim 1.

* * * * *